(12) United States Patent
Martinez et al.

(10) Patent No.: US 7,659,085 B2
(45) Date of Patent: Feb. 9, 2010

(54) METHODS AND COMPOSITIONS FOR THE SIMULTANEOUS DETECTION OF MULTIPLE ANALYTES

(75) Inventors: Joseph E. Martinez, McDonough, GA (US); George M. Carlone, Stone Mountain, GA (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 1167 days.

(21) Appl. No.: 10/259,907

(22) Filed: Sep. 27, 2002

(65) Prior Publication Data

US 2003/0027205 A1 Feb. 6, 2003

Related U.S. Application Data

(63) Continuation of application No. PCT/US01/09576, filed on Mar. 26, 2001.

(60) Provisional application No. 60/192,712, filed on Mar. 28, 2000.

(51) Int. Cl.
 *G01N 33/554* (2006.01)
(52) U.S. Cl. .......................... 435/7.32; 435/6; 435/7.1; 435/7.2; 435/7.92; 435/38; 435/971; 435/973; 436/63; 436/518; 436/523; 436/524; 436/528; 436/537; 436/10; 436/56; 436/164; 436/172
(58) Field of Classification Search ............. 435/6, 435/7.1, 7.2, 7.92, 7.94, 971, 973, 7.32, 38, 435/287.2; 436/500, 506, 517, 518, 523–534, 436/546, 56, 164, 811, 172, 548, 537, 10
See application file for complete search history.

(56) References Cited

U.S. PATENT DOCUMENTS

| | | | | |
|---|---|---|---|---|
| 5,798,217 | A * | 8/1998 | Bolton et al. | 435/7.23 |
| 6,280,618 | B2 * | 8/2001 | Watkins et al. | 210/222 |
| 6,524,793 | B1 * | 2/2003 | Chandler et al. | 435/6 |

2003/0008410 A1  1/2003  Hechinger

FOREIGN PATENT DOCUMENTS

| WO | WO 99/36564 | 7/1999 | |
|---|---|---|---|
| WO | WO 99/64867 | * 12/1999 | ............ 435/7.2 |

OTHER PUBLICATIONS

Martinez et al. A Flow Cytometric Opsonophagocytic Assay for Measurement of Functional Antibodies after Vaccination with th 23-valent Pneumococcai Polysaccharide Vaccine (Clinical and Diagnostic Laboratory Immunology 6 (4): 581-586 (Jul. 1999)).*

Carson et al. Simultaneous quantitation of 15 cytokines using multiplexed flow cytometry assay (Journal of Immunological Methods 227: 41-52 (1999)).*

Carson et al., "Simultaneous Quantitation of 15 Cytokines Using a Multiplexed Flow Cytometric Assay", *Journal of Immunological Methods*, Apr. 21, 1999, pp. 41-52, © 1999 Elsevier Science B.V.

Kettman et al., "Classificiation and Properties of 64 Multiplexed Microsphere Sets", *Cytometry*, Jun. 10, 1998, pp. 234-243, Cytometry 33 © 1998 Wiley-Liss, Inc.

Park et al., "A Latex Bead-Based Row Cytometric Immunoassay Capable of Simultaneous Typing of Multiple Pneumococcal Serotypes (Multibead Assay)", *Clinical and Diagnostic Laboratory Immunology*, May 2000, pp. 486-489, vol. 7, No. 3, © 2000, American Society of Microbiology.

Martinez et al., "A Flow Cytometric Opsonophagocytic Assay for Measurement of Functional Antibodies Elicited after Vaccination with the 23-Valent Pneumococcal Polysaccharide Vaccine", *Clinical and Diagnostic Laboratory Immunology*, Jul. 1999, pp. 581-586, vol. 6, No. 4.

* cited by examiner

*Primary Examiner*—Gailene R Gabel
(74) *Attorney, Agent, or Firm*—Gifford, Krass, Sprinkle, Anderson & Citkowski, P.C.

(57) ABSTRACT

Methods and compositions comprising immunoassays for the detection of antigens and antibodies in a sample are described. In particular, the present invention provides assays that are useful for the rapid and simultaneous detection of multiple different antigens and antibodies. In preferred embodiments, the assays include fluorescent labels of multiple wavelengths or intensities, which are used to label the antigens and antibodies directly and to label beads coated with molecules specific for the antigen or antibody. The detection of a fluorescence shift indicates the presence or identity of the antigen or antibody in the sample.

10 Claims, 5 Drawing Sheets

Figure 4: Example of dilutions demonstrating loss of reactivity to C. pneumoniae antigen as antibody in serum sample is diluted, allowing titration of antibodies specific for C. pneumoniae. In this example, the reported titer is 512 (set with cutoff of 20% greater than 2nd antibody control.

METHODS AND COMPOSITIONS FOR THE SIMULTANEOUS DETECTION OF MULTIPLE ANALYTES

This is a continuation of PCT/US01/09576, filed Mar. 26, 2001, which claims the benefit of U.S. Provisional Application No. 60/192,712, filed Mar. 28, 2000.

This invention was made by the Centers for Disease Control and Prevention, an agency of the United States Government. Therefore, the United States Government has certain rights in this invention.

FIELD OF THE INVENTION

The present invention relates to the field of immunologic detection of multiple analytes.

BACKGROUND OF THE INVENTION

*Streptococcus pneumoniae* is one of the three leading causes of bacterial meningitis and the most common cause of bacterial pneumonia. Although *S. pneumoniae* is carried by 10-30% of normal individuals without incidence, alcoholism, diabetes mellitus, chronic renal disease, and smoking are associated with more frequent and serious pneumococcal pneumonia. Pneumococcal pneumonia begins abruptly with a shaking chill and high fever. Cough with production of sputum pink to rusty in color and pleuritic chest pain are also common. Those who survive without therapy suffer from a sustained fever, plueritic pain and reproductive cough that continue until a "crisis" occurs 5-10 days after the onset of the disease. The "crisis" is actually associated with effective levels of opsonizing antibodies reaching the lesion.

Pneumococcal infection has been treated in the past with penicillin and other β-lactam agents. However, in the last 15 years, strains have developed that show resistance to both penicillin and cephalosporin. Due to the rise in drug resistance, pneumococcal epidemiologic and vaccine development studies have become increasingly important. Since epidemiologic and vaccine development studies require the evaluation of carriage and serotype identification, methods of serotyping have also become increasingly important. The current method of serotyping individual isolates is a manual assay that is both time consuming and subjective. What is needed in the art, is an automated, rapid and objective method of serotyping *S. pneumoniae* and other pathogens.

Chlamydia are obligate intracellular bacteria of which four species of are known: *C. pneumoniae, C. psittaci, C. pecorum* and *C. trachomatis. C. pneumoniae* is implicated as a causative or additive agent in coronary artery disease (CAD). *C. psittaci* causes psittacosis or ornithosis which is contracted through inhalation of respiratory secretions or dust from droppings of infected birds. *C. pecorum*, on the other hand, is currently believed not to infect humans. With better ability to detect different species of Chlamydia, these accepted paradigms regarding the different species may change or be enlarged.

The more widely known Chlamydia species, *Chlamydia trachomatis*, is the most common bacterial sexually transmitted disease (STD) in the United States today. The U. S. Centers for Disease Control and Prevention estimates that more than four million new cases occur each year. The highest rates of *C. trachomatis* infection are in 15- to 19-year-old adolescents regardless of demographics or location. Pelvic inflammatory disease (PID), a serious complication of *C. trachomatis* infection, has emerged as a major cause of infertility among women of childbearing age. *C. trachomatis* can be transmitted during vaginal, oral, or anal sexual contact with an infected partner. A pregnant woman may pass the infection to her newborn during delivery, with subsequent neonatal eye infection or pneumonia. The annual cost of *C. trachomatis* infection is estimated to exceed two billion dollars.

Most chlamydial infections are silent, causing no symptoms. This makes infection with Chlamydia species especially harmful because the bacteria normally cause serious, and possibly permanent, health impairment by the time the infected individuals realize they have been infected. It is only after CAD has developed or infertility is found that infected persons discover they have been infected with Chlamydia bacteria.

For example, *C. trachomatis* is transmitted silently by sexual contact. Persons infected with *C. trachomatis* may experience abnormal genital discharge or pain during urination. These early symptoms may be mild. If symptoms occur, they usually appear within one to three weeks after exposure. Two of every three infected women and one or two of every four infected men have no symptoms whatsoever. As a result, often the disease may not be diagnosed and treated until complications develop. It is estimated that, in women, one-third of the *C. trachomatis* infections result in PID. Often these infections are not diagnosed until PID or other complications develop. In men, rarely, *C. trachomatis* infections may lead to pain or swelling in the scrotal area, which is a sign of epididymitis, an inflammation of a part of the male reproductive system located near the testicles. Left untreated, this condition, like PID in women, can cause infertility. *C. trachomatis* can also cause proctitis (inflamed rectum) and conjunctivitis (inflammation of the lining of the eye). The bacteria also have been found in the throat as a result of oral sexual contact with an infected partner. In tropical climates, a particular strain of *C. trachomatis* causes an STD called lymphogranuloma venereum (LGV), which is characterized by prominent swelling and inflammation of the lymph nodes in the groin. Complications may follow if LGV is not treated. This infection is currently very rare in the United States, though with the expansion of tropical diseases into the continental U.S., more cases may be seen in the future.

*C. trachomatis* infection can be confused with gonorrhea because the symptoms of both diseases are similar. The most reliable way to diagnose *C. trachomatis* infection is for a clinician to send a sample of secretions from the patient's genital area to a laboratory that will look for the *C. trachomatis* organism using one of a wide variety of quick and inexpensive laboratory tests. Although attempting to grow the organism in specialized tissue culture in the laboratory is one of the most definitive tests, it is expensive and technically difficult to perform, and test results are not available for three or more days.

Other test formats exist that provide more rapid diagnosis of *C. trachomatis*, but there are no tests available to distinguish between various species of Chlamydia. Once an infected person has been diagnosed with an impairment, such as CAD or PID, the current practice is to attribute the damage to a species of Chlamydia, based on the location of the impairment. For example, PID would suggest *C. trachomatis* infection, and CAD would suggest *C. pneumoniae* infection.

If an active infection with *C. trachomatis* is found, antibiotics are prescribed, such as a one-day course of azithromycin or a seven-day course of doxycycline. Other antibiotics such as erythromycin or ofloxacin also are effective. Pregnant women can be treated with azithromycin or erythromycin. Amoxicillin is also a safe alternative for treating pregnant women. Penicilin, which is often used for treating some other STDs, is not effective against *C. trachomatis* infections.

The ease of treatment of active *C. trachomatis* infection emphasizes the need to be able to diagnose infection by Chlamydial bacteria. If the Chlamydial species can be easily diagnosed, the damage due to infection can be prevented. Additionally, the ability to diagnose which species of Chlamydia the person has or has had can aid in treatment because the affected organs, such as the heart or fallopian tubes, can be more carefully examined for damage and more complete treatment can be provided.

The inability to determine the presence or past presence of different Chlamydia species bacteria has many costs, both nationally and individually. Each year up to one million women in the United States develop PID. As many as half of all cases of PID may be due to *C. trachomatis* infection, and many of these occur without symptoms. PID can result in scarring of the fallopian tubes, which can block the tubes and prevent fertilization from taking place. An estimated 100,000 women each year become infertile as a result of PID. In other cases, scarring may interfere with the passage of the fertilized egg down into the uterus. When this happens, the egg may implant in the fallopian tube, causing an ectopic or tubal pregnancy. This condition may be life threatening for the mother and may result in the loss of the fetus. PID is the most common cause of pregnancy-related death among poor teenagers in the inner cites and rural areas of the United States. The annual cost estimates exceed seven billion dollars.

What is needed are rapid and accurate tests that can differentiate the different species of Chlamydia. At the present time, though some tests exist for *C. trachomatis*, there may be many infections due to other species of Chlamydia that go undiagnosed and untreated. Additionally what is needed are tests that can determine the species of Chlamydia that previously infected the patient in order to track the progression of such infection.

SUMMARY OF THE INVENTION

The present invention relates to specific immunoassays for the detection of multiple analytes such as antigens and antibodies in a sample, and addresses the continuing need for rapid, and automated methods of simultaneously testing for and detecting multiple pathogens. In one embodiment of the present invention, the immunoassay allows the simultaneous detection and differentiation of multiple antigens in a sample through the use of a plurality of fluorescent bead sets and a secondary label. In an alternate embodiment, the present invention provides an immunoassay for the simultaneous detection and differentiation of multiple antibodies in a sample using a plurality of fluorescent bead sets and a secondary label. In a preferred embodiment, the secondary labels are fluorescent and the fluorescent beads and secondary labels are detected using a flow cytometer.

Accordingly, it is an object of the present invention to provide methods and compositions for the simultaneous detection of antigens derived from multiple pathogenic species, serotypes or strains, particularly *Streptococcus*.

It is another object of the present invention to provide methods and compositions for the simultaneous detection of antibodies directed toward multiple pathogenic species, serotypes or strains, particularly Chlamydia.

It is yet another object of the present invention to provide simple yet accurate methods and compositions that can be used to aid in the diagnosis or prognosis of a disease or infection.

It is yet another object of the present invention to provide methods and compositions for the rapid and automated measurement of antibody titers.

These and other objects, features and advantages of the present invention will become apparent after a review of the following detailed description of the disclosed embodiments and the appended claims.

DETAILED DESCRIPTION

Figure 1:
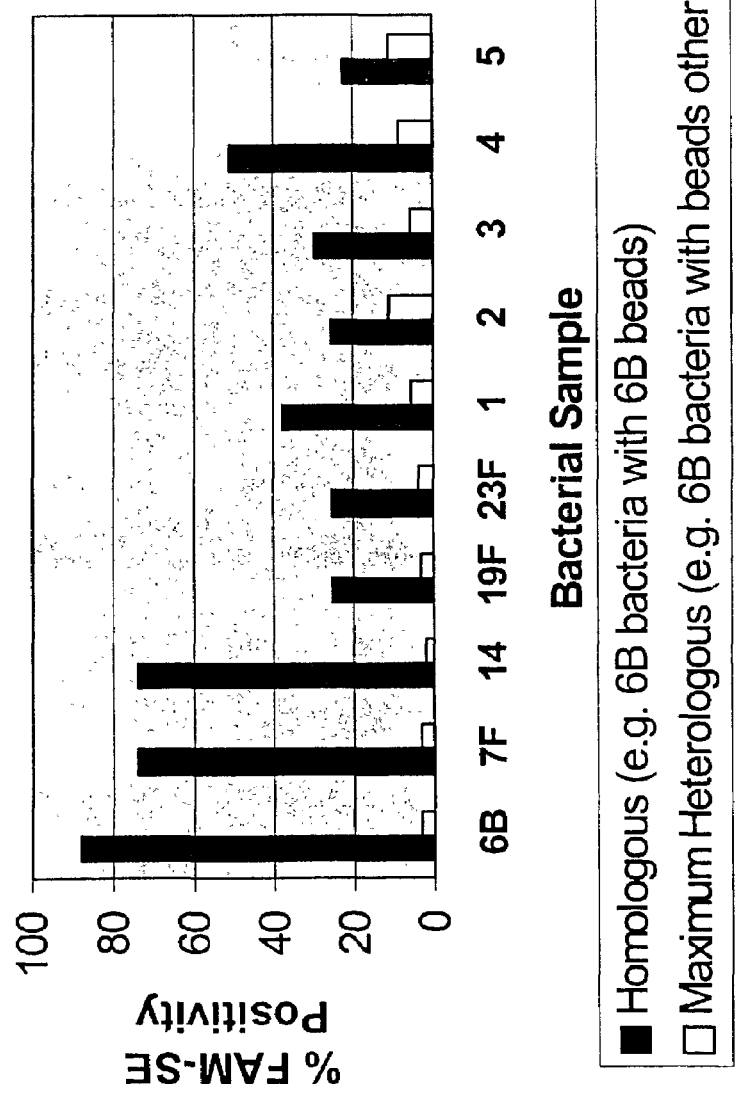
FIG. 1 is a graph showing flow cytometric analysis of *S. pneumoniae* that demonstrates the specificity of various serotype-specific beads.

The present invention provides rapid, automated, and specific immunoassays for the detection of antigens and antibodies in a sample. In one embodiment of the present invention, the immunoassay allows the simultaneous detection and differentiation of multiple antigens in a sample through the use of a plurality of different fluorescent beads and a secondary label. In an alternate embodiment, the present invention provides an immunoassay for the simultaneous detection and differentiation of multiple antibodies in a sample using a plurality of different fluorescent beads and a secondary label. In a preferred embodiment, the secondary label is fluorescent and the fluorescent beads and secondary labels are detected using a flow cytometer.

Multiple antigens in a single sample may be simultaneously detected and distinguished using the present invention. The present invention provides a method of simultaneously detecting and distinguishing different antigens in a sample, comprising, combining a sample suspected of containing antigens with a plurality of different fluorescent beads bound to different binding molecules specific for the antigens, labeling the antigens with a second label, and detecting the formation of a complex comprising the fluorescent bead, binding molecule and the labeled antigen. In a preferred embodiment, the antigen is labeled with a second fluorescent label that differs from the fluorescent bead, but has fluorescence compatible with the fluorescent bead. In a more preferred embodiment, the measurement of fluorescence is made by use of a flow cytometer. In a further preferred embodiment, the measurement of fluorescence is made by determining the ratio of the fluorescence of the two or more fluorescent dyes. Measurement of the ratio removes the undesired effect of clumping or aggregating of the beads. It is a surprising finding of the present invention that a plurality of different fluorescent labels can be used simultaneously in a flow cytometer without significant interference among the labels.

As used herein, the term "antigen" refers to an entity or fragment thereof that can induce an immune response in a mammal. The term includes a viable or non-viable intact pathogen or peptides, nucleic acids, polysaccharides, or lipids derived from a pathogen. The antigens to be detected may be bacterial, viral, fungal or parasitic in nature, however in a preferred embodiment, the antigens are bacterial antigens. In a preferred embodiment, the antigens are derived from *Streptococcus pneumonia*. However, the present invention is not limited by the specific pathogenic organisms herein described. The present invention contemplates the detection of antigens derived from any pathogen that can be detected by the methods and compositions of the present invention. Notably, unlike prior art assays that utilize only viable bacteria, the present method allows for the detection of non-viable bacteria and thus reduces the health risk to an individual performing the assay.

The antigens detected using the present invention may be contained in a biological sample, such as a body fluid or tissue, or an environmental sample. The term "body fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions. In a preferred embodiment, the antigens are contained in serum, whole blood or sputum swab samples. As used herein, the term "environmental sample" includes soil and water samples.

Additionally, "binding molecule(s)" may include, but are not limited to, antibodies, receptors or lectins. In a preferred embodiment, the binding molecules specific for the antigens are antibodies. As used herein, the terms "antibody" and "antibodies" include monoclonal antibodies, polyclonal, chimeric, single chain, bispecific, simianized, and humanized antibodies as well as Fab fragments, including the products of an Fab immunoglobulin expression library. The antibodies may be specific for any immunogen including but not limited to a peptide, nucleic acid, polysaccharide or lipid. The phrases "specifically binds to", "specific for" or "specifically immunoreactive with", when referring to an antibody, refer to a binding reaction which is determinative of the presence of the peptide in the presence of a heterogeneous population of proteins and other biologics. Thus, under designated immunoassay conditions, the specified binding molecules bind preferentially to a particular peptide and do not bind in a significant amount to other proteins present in the sample. Specific binding to a peptide under such conditions requires a binding molecule that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity. In a preferred embodiment, the binding molecules of the present invention are specific for antigens derived from *Streptococcus pneumonia*.

The immunoassay described herein permits the simultaneous detection and distinguishment of several antigens in a single sample through the use of a plurality of different fluorescently labeled beads. The present invention provides a method of creating bead sets wherein each bead in the set has a different fluorescence and is also bound to a binding molecule with a different specificity such that a particular fluorescence corresponds with a particular antibody specificity. Also provided is a method of labeling the antigen in the sample with a second fluorescent molecule. The term "second" merely indicating that the fluorescence is different from the fluorescent molecules labeling the beads. Labeling the beads and antigen in such a manner allows for detection of the antigen in the sample by detection of a shift in fluorescence.

A shift in fluorescence in a second fluorescence wavelength or intensity is created upon the binding of the fluorescently labeled bead-binding molecule complex to the fluorescently labeled antigen. Different antigens in a single sample may be distinguished because each type of bead-binding molecule complex fluoresces differently, and is specific for a different antigen. The difference in the fluorescence between each type of complex arises due a difference between emission spectra and/or the fluorescence intensity between each bead type and between the beads and labeled antigens. In an alternate embodiment, the fluorescence emission spectra and/or intensities of each labeled antigen also differ between themselves.

For example, in one embodiment of the present invention, antigens from three different serotypes of a single pathogenic species are simultaneously detected and distinguished, preferably in a flow cytometer, by labeling the bead-antibody complexes specific for each antigen with different fluorescent colors, and labeling each antigen with the same fluorescent color, but with a color that differs from the fluorescent colors labeling the beads. In an alternate embodiment, the bead-binding molecule complexes are labeled with the same fluorescent color, but with different fluorescent intensities that are distinguished, preferably in a flow cytometer, and each antigen is labeled with the same fluorescent color or intensity, but with a color or intensity that differs from the bead-binding molecule complex. In yet another embodiment, the fluorescence between each bead, between the beads and the antigens, and between the antigens differs either in wavelength or intensity.

The method provided herein also includes the option for measurement of antigens using other labels that function as the herein-described fluorescent labels or fluorescent beads. Additionally, the present invention comprises detection of the label by methods known to those skilled in the art, though the preferred methods of detection comprise the use of a flow cytometer. It is well within the knowledge of those skilled in art to use alternative labels, whether fluorescent, radioactive, bioluminescent, chemiluminescent, chemical, enzymatic or others known to those skilled in the art, to provide detection of antigens using the methods and compositions of the present invention. Furthermore, use of alternative labels may call for a specific detection apparatus. It is also to be understood that the present method is not limited by the type of bead used, as beads useful for attachment of antibodies are known to those skilled in the art, and any structure that is capable of binding antibody and functioning as the beads described herein is encompassed by the present invention. The fluorescent beads may be, but are not limited to, latex beads, polystyrene beads and magnetic beads, however polystyrene beads are preferred.

In a preferred method of the present invention, the antigens contained in the sample are fluorescently labeled. The antigens may be labeled prior to or following their combination with the fluorescent beads depending on the type of fluorescent label employed. In one embodiment, fluorescent labels are directly attached to the antigens. In another embodiment, the antigens are labeled with a fluorescent antibiotic. In yet a third embodiment, the antigens are labeled with a fluorescent DNA binding dye such as AAD, EMA, and PI. In a fourth embodiment, the antigens are labeled with a secondary antibody that is specific for the antigen. The secondary antibody may be fluorescent or may be bound to an enzyme such as alkaline phosphatase. When the secondary antibody is bound to alkaline phosphatase, the bound antigens are fluorescently labeled by the addition of ELF-97 dye (Molecular Probes, Eugene, Oreg.) prior to detection. More specifically, the alkaline phosphatase is used to enzymatically cleave a soluble non-fluorescent dye, resulting in a non-soluble and fluorescent dye. In each embodiment, the antigens in the sample are labeled with a fluorescent label that is different than the fluorescent label attached to the beads. The antigens and beads may differ by their fluorescence emission wavelengths, their fluorescence intensities, or a mixture of both. It is also to be understood that the different antigens in the sample may be labeled the same or differently from each other. In a preferred embodiment, all antigens in a single sample are labeled with the same secondary fluorescent molecules. Additionally, due to the fact that detection of the antigen is based upon a shift in the fluorescence of a single complex, the removal of unbound secondary label is unnecessary.

The fluorescent molecules described above as used for the labeling of the beads and antigens of the present invention may include, but are not limited to, fluorescein and its derivatives such as 5, 6, carboxyfluorescein succinimidyl ester, or other dyes such as ethidium monoazide (EMA), phycoerythrin, allo-phycocyanin, phycocyanin, rhodamine, tetramethyl-rhodamine, Texas Red, EDANS, BODIPY dyes, Cy3 and Cy5, FITC, FAM, or TAMRA. It is to be understood that the fluorescent molecule used to label the antigen is compatible with the fluorescent molecule used to label the beads.

Other important terms as used herein are as follows. The terms "a", "an" and "the" are defined to mean one or more and include the plural unless the context is inappropriate. The terms "detecting" or "detection" refer to qualitatively or quantitatively determining the presence of the biomolecule under investigation. The term flow cytometer is used herein for any apparatus which creates a single file flow of particles within a fluid and measures fluorescence of the particles. The sample fluid can be constrained with a narrow flow channel or by hydrodynamic focussing with a sheath fluid.

The method of simultaneously detecting multiple antigens in a single sample as provided herein has many uses. The method may be used to determine whether a particular individual is a carrier of a pathogen and more particularly, may be used to simultaneously determine the serotype of the pathogen. Accordingly, the present method may be used for the diagnosis or prognosis of a disease. The method of the present invention may also be used to simultaneously determine if the individual is infected with more than one pathogen or more than one serotype or strain of a particular pathogen. Importantly, the present invention provides a rapid, automated and accurate means for detecting multiple serotypes or species of pathogens. In a preferred embodiment, the pathogen is a bacteria, and in a more preferred embodiment, the bacteria is *Streptococcus pneumoniae*.

In an alternate embodiment of the present method, multiple antibodies in a single sample may be simultaneously detected and distinguished. The present invention provides a method of simultaneously detecting and distinguishing different antibodies in a sample, by combining a sample suspected of containing antibodies with a plurality of different fluorescent beads bound to different antigens, labeling the antibodies with a second label, and detecting the formation of a complex comprising the fluorescent bead, antigen and labeled antibody. A complex is formed between the bead, antigen and antibody whereupon the antibody in the sample is specific for the antigen attached to the bead. In a preferred embodiment, the antibody is labeled with a second fluorescent label that differs from the fluorescent bead. In a more preferred embodiment, the measurement of the fluorescence is made by use of a flow cytometer. It is a surprising finding of the present invention that a plurality of different fluorescent labels can be used simultaneously in a flow cytometer without significant interference among the labels.

As mentioned above, the terms "antibody" and "antibodies" as used herein include monoclonal antibodies, polyclonal, chimeric, single chain, bispecific, simianized, and humanized antibodies as well as Fab fragments, including the products of an Fab immunoglobulin expression library. The antibodies may be specific for any antigen including but not limited to a peptide, nucleic acid, polysaccharide or lipid. The phrases "specifically binds to", "specific for" and "specifically immunoreactive with", when referring to an antibody, refer to a binding reaction which is determinative of the presence of the peptide in the presence of a heterogeneous population of proteins and other biologics. Thus, under designated immunoassay conditions, the specified antibodies bind preferentially to a particular peptide and do not bind in a significant amount to other proteins present in the sample. Specific binding to a peptide under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity. In a preferred embodiment, the antibodies of the present invention are specific for antigens derived from a Chlamydia species. In a further preferred embodiment, the antigens are derived from a Chlamydia species selected from the group consisting of *C. pneumoniae, C. psittaci, C. pecorum* and *C. trachomatis*. Most preferably, the antigens are *C. trachomatis* antigens.

The antibodies detected using the method described herein may be contained in a biological sample, such as a body fluid or tissue. The term "body fluid," as used herein, includes, but is not limited to, saliva, gingival secretions, cerebrospinal fluid, gastrointestinal fluid, mucous, urogenital secretions, synovial fluid, blood, serum, plasma, urine, cystic fluid, lymph fluid, ascites, pleural effusion, interstitial fluid, intracellular fluid, ocular fluids, seminal fluid, mammary secretions, and vitreal fluid, and nasal secretions. In a preferred embodiment, the antibody is contained in serum, whole blood or sputum swab samples.

The present invention permits the simultaneous detection and distinguishment of several antibodies in a single sample through the use of a plurality of fluorescently labeled beads. The present invention provides a method of creating bead sets wherein each bead in the set has a different fluorescence and is also bound to a different antigen such that a particular fluorescence corresponds with a particular antigenic specificity. Also provided is a method of labeling an antibody in a sample with a second fluorescent molecule. The term "second" merely indicating that the fluorescence is different from the fluorescent molecules labeling the beads. Labeling the beads and antibody in such a manner allows for detection of the antibody in the sample by detection of a shift in fluorescence. The antibody in the sample may be labeled with a fluorescent molecule in a variety of manners, however in a preferred embodiment, the antibody in the sample is labeled with a secondary antibody that is fluorescently labeled such as an anti-IgA, anti-IgD or anti-IgM antibody. More preferably, the secondary antibody is an anti-IgG fluorescently-labeled antibody.

A shift in fluorescence to a third fluorescence wavelength or intensity is created upon the binding of the fluorescently labeled bead-antigen complex to the fluorescently labeled antibody. Different antibodies in a single sample may be distinguished because the bead-antigen complexes specifically recognized by each antibody fluoresce differently. The difference in the fluorescence between each type of complex arises due a difference between emission spectra and/or the fluorescence intensity between each bead type and between the beads and labeled antibodies. In an alternate embodiment, the fluorescence emission spectra and/or intensities of each labeled antibody also differ.

For example, in one embodiment of the present invention, antibodies specific for three different species of a pathogen are simultaneously detected and distinguished, preferably in a flow cytometer, by labeling the bead-antigen complexes with different fluorescent colors, labeling each antibody with the same fluorescent color, but with a color that differs from the fluorescent colors labeling the beads. In an alternate embodiment, the bead-antigen complexes are labeled with the same fluorescent color, but with different fluorescent intensities that are distinguished, preferably in a flow cytometer, and each antibody is labeled with the same fluorescent color or intensity, but with a color or intensity that differs from the bead-antigen complex. In yet another embodiment, the fluorescence between each bead, between the beads and the antibodies, and between the antibodies differs. It is to be understood that the present invention is not limited by the type of bead used, as beads useful for attachment of antigens are known to those skilled in the art, and any structure that is capable of binding antigen and functioning as the described beads herein is encompassed by the present invention. The fluorescent beads may be, but are not limited to, latex beads, polystyrene beads and magnetic beads, however polystyrene beads are preferred.

The present invention also comprises measurement of antibodies using other labels that function as the herein-described fluorescent labels or fluorescent beads. Additionally, the present invention comprises detection of the label by methods known to those skilled in the art, though the preferred methods of detection comprise use of a flow cytometer. It is well within the knowledge of those skilled in art to use alternative labels, whether fluorescent, radioactive, bioluminescent, chemiluminescent, chemical, enzymatic or others known to those skilled in the art, to provide detection of antibodies using the methods and compositions of the present invention. Furthermore, use of alternative labels may call for a specific detection apparatus.

In a further embodiment of the present invention, the fluorescently labeled beads of the present invention bound to antigen are combined with a sample suspected of containing antibodies. The antibodies are subsequently fluorescently labeled with fluorescent molecules, for example, fluorescein and its derivatives such as 5, 6, carboxyfluorescein succinimidyl ester, or other dyes such as ethidium monoazide (EMA), phycoerythrin, allo-phycocyanin, phycocyanin, rhodamine, tetramethylrhodamine, Texas Red, EDANS, BODIPY dyes, Cy3 and Cy5, FITC, FAM, or TAMRA. It is to be understood that the fluorescent molecule used to label the antibody is compatible with the fluorescent molecule used to label the beads. In another embodiment, the antibodies in the sample are labeled with fluorescent molecules prior to the combination of the sample and the fluorescently labeled bead-antigen complex.

In each of the above-described embodiments, the antibodies in the sample are labeled with a different fluorescent label than the beads. The antibodies and beads may differ by their fluorescence emission wavelengths, their fluorescence intensities, or a mixture of both. It is also to be understood that the different antibodies in the sample may be labeled the same or differently from each other. In a preferred embodiment, all antibodies in a single sample are labeled with the same secondary fluorescent molecules.

The method of simultaneously detecting multiple antibodies in a single sample as provided herein has many uses. The method may be used to determine whether a particular individual is or was a carrier of a pathogen. The present invention may also be used for the determination of antibody titers, for the study of immune responses and for the determination of vaccine efficacy. Accordingly, the present invention may be used as an aid in the diagnosis or prognosis of a disease. More particularly, the method of the present invention may be used to simultaneously detect the presence of an antibody response to a multitude of different pathogens, different pathogenic species, or different strains or serotypes of a single pathogenic species. Simultaneous detection of an antibody response to multiple pathogenic species is useful in situations wherein more than one species of a pathogen causes disease and/or wherein one species may be antibiotic resistant. The present method provides a rapid, automated and accurate means for detecting antibody responses to multiple serotypes or species of pathogens. In a preferred embodiment, the pathogen is a bacteria. In a more preferred embodiment, the bacteria is a Chlamydia species selected from the group consisting of *C. pneumoniae*, *C. psittaci*, *C. pecorum* and *C. trachomatis*, and most preferably *C. trachomatis*.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Simultaneous Detection of Multiple Antigens Using Flow Cytometric Techniques

Monoclonal antibodies were each dissolved to a concentration of 20-50 µg/ml in 50 mM MES buffer (pH 6.0 2-[N-Morpholino]ethanesulfonic acid, FW 213.4) in a glass test tube, 1 ml protein solution. 100 µl of 2% aqueous suspension of carboxylate-modified microspheres was then added and incubated for 15 minutes at room temperature. For each different antibody, the carboxylate-modified microspheres differed either by size, fluorescence intensity, or ratio of fluorescent dyes. Measuring the ratio of the fluorescence of the two or more fluorescent dyes is preferred since this measurement removes the effect of clumping or aggregating of the beads. Subsequently, 4 mg of EDAC was added and mixed by vortexing. The pH was adjusted to 6.5±0.2 with dilute NaOH and the reaction mixture was incubated on a rocker or shaker at room temperature for two hours. Following incubation, glycine was added to a final concentration of 100 mM to quench the reaction. The solution was incubated an additional 30 minutes on a rocker or shaker.

To separate the antibody-labeled beads from the unreacted protein, the solution was centrifuged at 13,000 r.p.m. for 20 minutes and the supernatant was discarded. The antibody-labeled beads were then washed three times with HBSS+ with 0.2% albumin (opsono buffer). The pellet was re-suspended in 1 ml of opsono buffer with antibiotics and stored at 4° C. in the dark until use. When multiple bead populations were used for the simultaneous detection of multiple antigens, the various bead populations were consolidated in 1 ml of opsono buffer, and stored.

For serotyping a *S. pneumoniae* bacterial solution, the suspension of bacteria approximated $1 \times 10^6$ bacteria per ml. 100 µl of the *S. pneumoniae* bacterial suspension was placed into appropriately labeled wells on 96 well plate and 20 µl of working bead solution was added to each well containing bacteria to be tested. The plate was incubated for 30 minutes at 37° C. with shaking. Following incubation, detection of bound *S. pneumoniae* bacteria was accomplished by adding a secondary fluorescent marker, FAM, which fluorescently labeled the bound bacteria. After incubation with dye, the beads were washed, re-suspended in opsono buffer and run on the cytometer.

Figure 3:
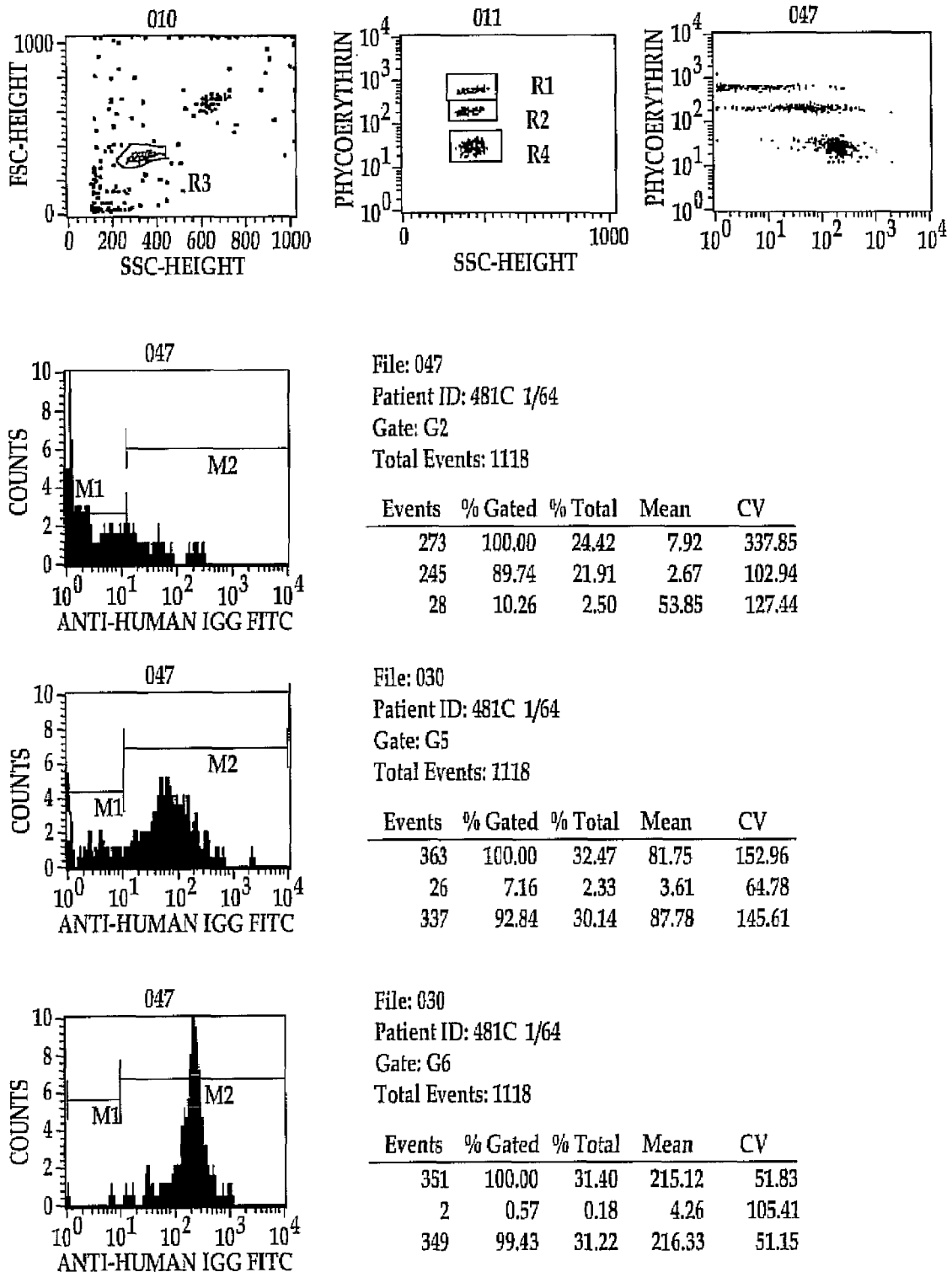
FIG. 3 is a series of histograms showing flow cytometric analysis of antibodies specific for either *C. trachomatis* antigen or *C. psittici* antigen that demonstrates simultaneous detection of both antibodies in a single sample.

The cytometer was set so that the bead population(s) were detected by their light scatter properties (forward angle light scatter, FALS, or orthogonal light scatter, SSQ). A gate was set around the singlet bead population. When the bead population contained sub-populations identified by different fluorescence intensities of a particular wavelength (FLI), a dot plot was created to display the gated bead populations by a light scatter parameter and a fluorescent parameter (FL1) as illustrated in FIG. 3. The presence of the bead-antibody-*S. pneumoniae* complexes were detected by a shift in the fluorescence signals in a second wavelength (FL2).

Figure 2:
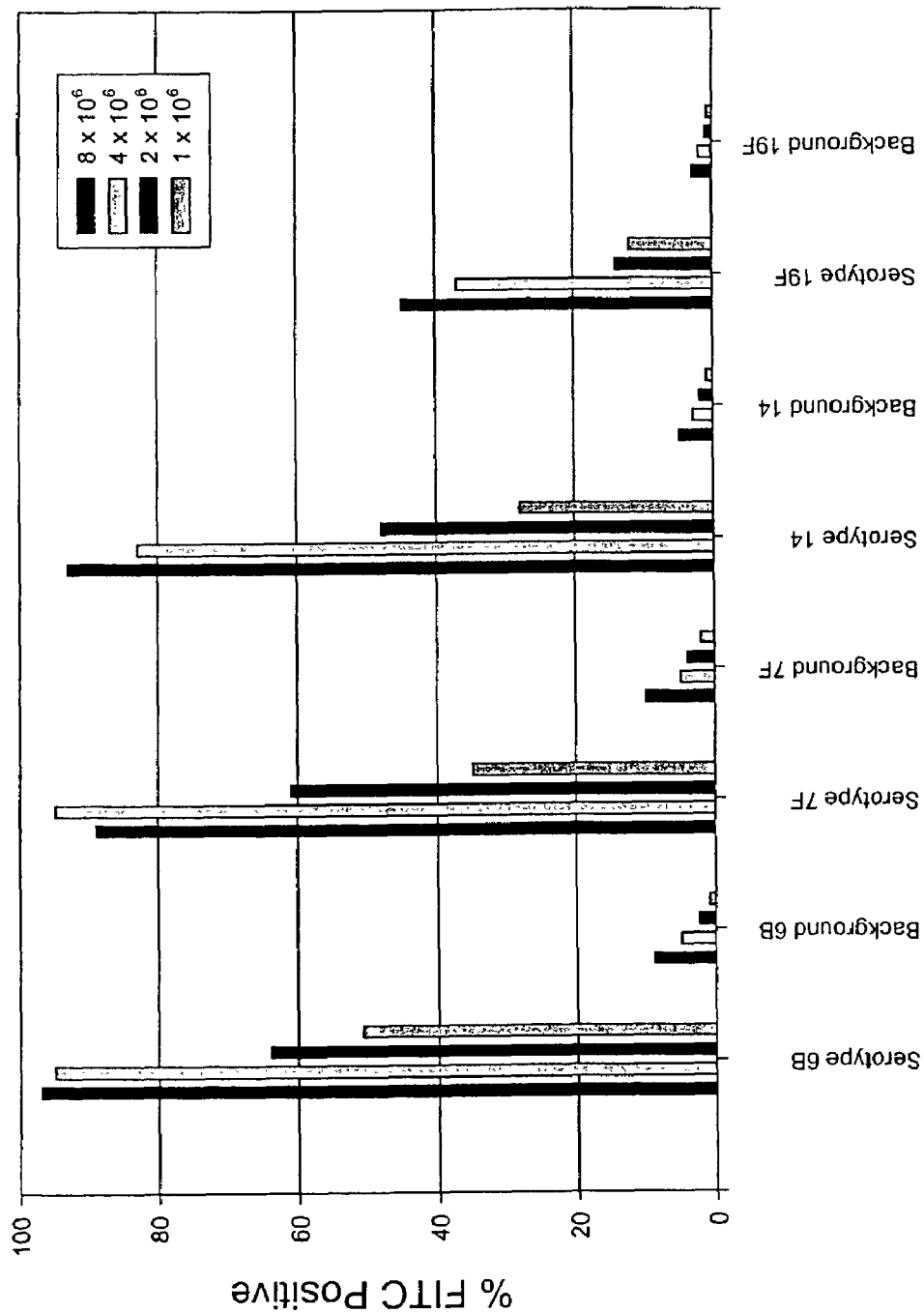
FIG. 2 is a graph showing flow cytometric analysis of *S. pneumoniae* at different bacterial concentrations that demonstrates the specificity of various serotype-specific beads.

As shown in FIGS. 1 and 2, the assay was capable of detecting the specific target serotype of each bead. FIG. 1 illustrates the difference in binding of specific target serotypes and non-specific serotype binding. For example, the 6B serotype specific bead demonstrated greater than 80% binding of fluorescent 6B serotype *S. pneumoniae* bacteria and less than 5% binding of the fluorescent non-6B pneumococci, 7F, 14, 19F and 23F serotypes. FIG. 2 illustrates the sensitivity of the assay in capturing specific fluorescent pneumococci. Specific and non-specific fluorescent pneumococci at different concentrations ranging from eight million to one million per milliliter were incubated with different capture beads. The results demonstrate excellent specificity of serotype binding and identification.

EXAMPLE 2

Simultaneous Detection of Multiple Antibodies Using Flow Cytometric Techniques

*C. pneumoniae, C. psittici* and *C. trachomatis* bacterial antigens were prepared for covalent linkage to carboxylate modified microspheres as follows. Suitable cell lines were separately infected with *C. pneumoniae, C. psittici* and *C. trachomatis* elementary bodies (EBs) and infection was tracked until the EBs were mature, but prior to cellular lysis. Cells were lysed to release the EBs, and the lysate was subjected to differential centrifugation to remove cellular debris and isolate purified EBs. This process was repeated until sufficient EBs were harvested for use in labeling beads. The number of EBs needed depended upon the amount of beads prepared. (For free growing bacterial pathogens, the above process may be skipped.)

Subsequently, separate suspensions of the *C. pneumoniae, C. psittici* and *C. trachomatis* organisms were made in Hank's Balanced Salt Solution (HBSS), at a concentration of approximately $1 \times 10^6$ organisms/µl. The organisms were inactivated by adding 100 µl of 10% buffered formalin solution, mixing and incubating for at least two hours. The organisms were centrifuged and pelleted and the supernatant was discarded. The organisms were re-suspended in 1 ml of HBSS and sonicated for one hour in a water bath type sonicator to completely disaggregate the organisms. Care was taken not to overheat the organisms during the sonication process, by adding a small amount of ice during the sonication process.

*C. pneumoniae, C. psittici* and *C. trachomatis* antigens were each separately dissolved to a concentration of 20-50 µg/ml in 50 mM MES buffer (pH 6.0 2-[N-Morpholino] ethanesulfonic acid, FW 213.4) in a glass test tube to a 1 ml protein solution. 100 µl of 2% aqueous suspension of carboxylate-modified microspheres was then added and incubated for 15 minutes at room temperature. For each different antigen, the carboxylate-modified microspheres differed either by size, fluorescence intensity, or ratio of fluorescent dyes. Subsequently, 4 mg of EDAC was added and mixed by vortexing. The pH was adjusted to 6.5±0.2 with dilute NaOH and the reaction mixture was incubated on a rocker or shaker at room temperature for two hours. Following incubation, glycine was added to a final concentration of 100 mM to quench the reaction. The solution was incubated an additional 30 minutes on a rocker or shaker.

To separate the Chlamydia antigen-labeled beads from the un-reacted protein, the solution was centrifuged at 13,000 r.p.m. for 20 minutes and the supernatant was discarded. The Chlamydia antigen-labeled beads were then washed three times with HBSS+ with 0.2% albumin (opsono buffer). The pellet was re-suspended in 1 ml of opsono buffer with antibiotics and stored at 4° C. in the dark until use. When multiple bead populations were used for the simultaneous detection of multiple antibodies, the various bead populations were consolidated in 1 ml of opsono buffer and stored.

For detection of specific antibodies, a serial dilution (1:8, 1:16, 1:32, etc.) of sera was prepared using opsono buffer. 10 µl of sera or a serial dilution was added to the appropriate well of a 96 well plate and 10 µl of working bead suspension was added. The working bead solution was a 1:40 dilution of well re-suspended stock bead solution in opsono buffer. Subsequently, 60 µl of opsono buffer was added. The final dilution in the first well was 1:8, 1:16 in second well, etc. The sera and bead solution was then incubated for 30 minutes at 37° C. with shaking.

Following incubation, bound antibodies were detected using a FITC anti-human IgG secondary antibody and a flow cytometer. The cytometer was set so that the bead population(s) were detected by their light scatter properties (forward angle light scatter, FALS, or orthogonal light scatter, SSQ). A gate was set around the singlet bead population. When the bead population contained sub-populations identified by different fluorescence intensities of a particular wavelength (FLI), a dot plot was created to display the gated bead populations by a light scatter parameter and a fluorescent parameter (FL1) as illustrated in FIG. 3. The presence of the Chlaymdia antigen-bead-antibody complexes were detected by a shift in the fluorescence signals in a second wavelength (FL2).

As shown in FIG. 3, three bead populations were identified by their different fluorescent intensities measured at 575 nm. Each bead population was coated with antigens isolated from a different Chlamydial species. Thus, each bead served to identify the presence of human antibodies directed to its specific Chlamydial species. The three beads were mixed to allow for simultaneous measurement of antibodies to each Chlamydial species. FIG. 3 is an example of a Chlamydia assay measuring human IgG reacting with *C. trachomatis* antigens, and to a lesser extent, reacting with *C. psittici*.

Additionally, *C. pneumoniae* labeled beads were produced as described above for *C. pneumoniae, C. psittici* and *C.*

Figure 4:
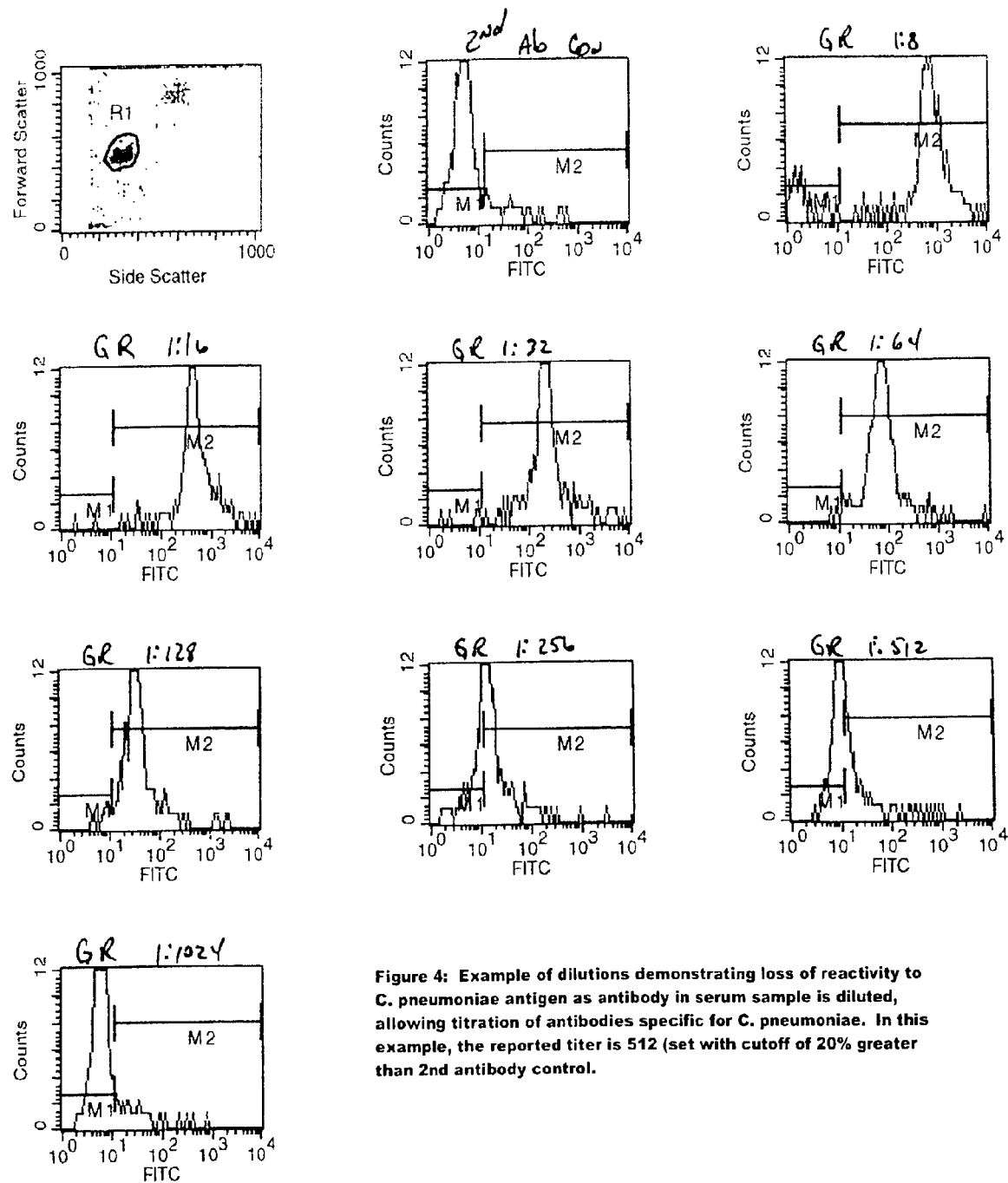
FIG. 4 is a series of histograms showing flow cytometric analysis of antibody specific for *C. pneumoniae* antigen that demonstrates loss of reactivity upon dilution of the antibody.
Figure 5:
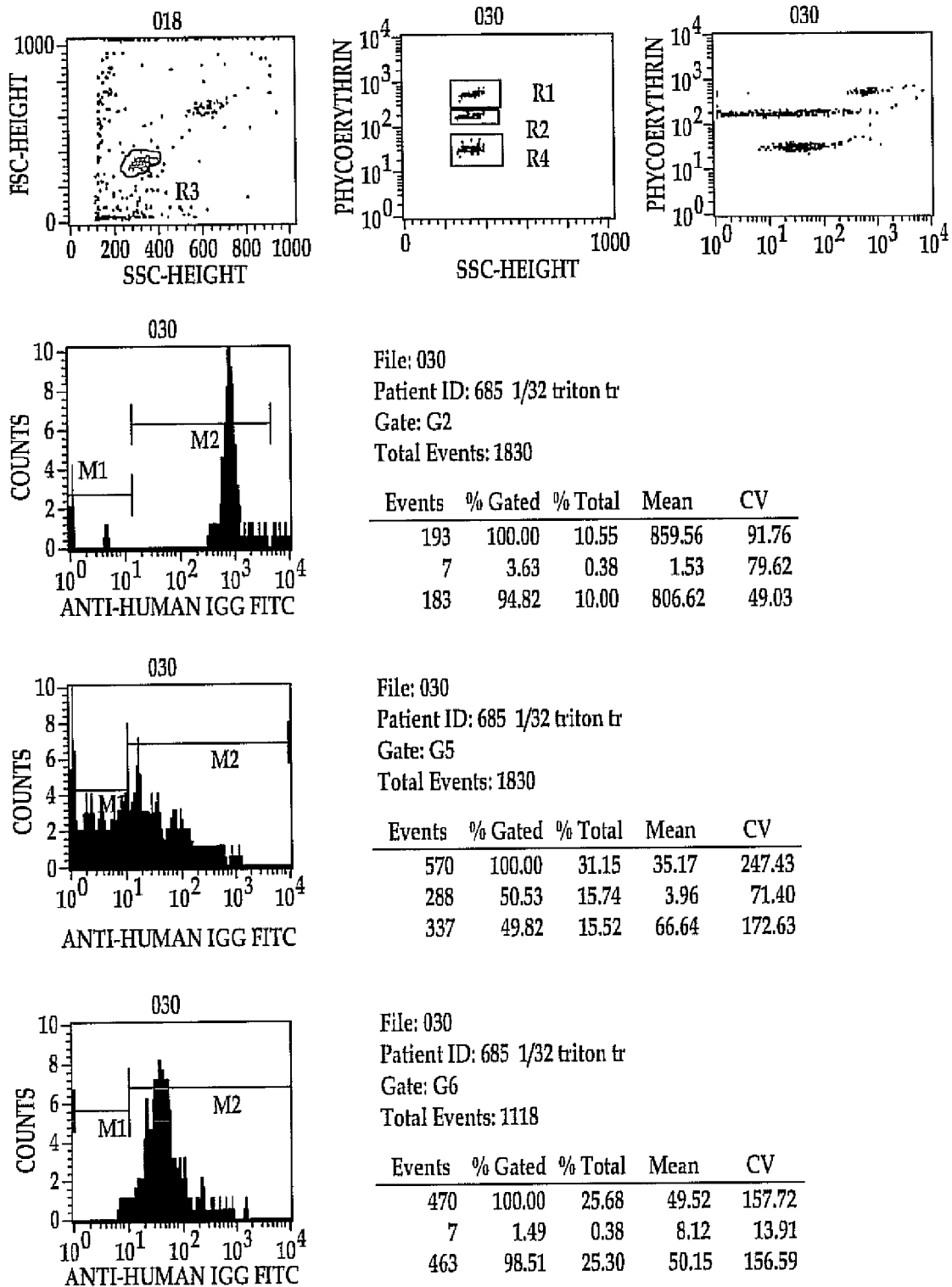
FIG. 5 is a series of histograms showing flow cytometric analysis of antibodies specific for *C. pneumoniae* antigen, *C. trachomatis* antigen and *C. psittici* antigen that demonstrates simultaneous detection of each antibody in a single sample.

*trachomatis* and used to determine the titer of antibodies specific for *C. pneumoniae*. As shown in FIG. 4, by serial dilution of a test serum, and subsequent testing of the diluted sera, it was possible to measure a titer of the specific antibody present in the sample. In this instance, the titer was 512 (set with a cutoff of greater than 20% above negative control). FIG. 5 demonstrates the reactivity of a *C. pneumoniae* reactive serum sample with minimal reactivity for *C. trachomatis* and *C. psittici* beads.

Modifications and variations of the present method will be obvious to those skilled in the art from the foregoing detailed description. Such modifications and variations are intended to come within the scope of the appended claims.

What is claimed is:

1. A method of simultaneously detecting and distinguishing a plurality of antigens in a sample, comprising:
   (a) combining a sample comprising a plurality of antigens with a plurality of different fluorescent antibody-bead complexes wherein each antibody specifically binds to an antigen if present in said sample, wherein each member of the plurality of fluorescent antibody-bead complexes comprises a different antibody and a different first fluorescent label,
   (b) labeling said antigens with a second fluorescent label that differs from any of the first fluorescent labels to create a plurality of fluorescent antigens, wherein the antigens are labeled with the second fluorescent label prior to or following their combination with the antibody-bead complexes; and
   (c) detecting and distinguishing the plurality of different antigens in the sample by observing a shift in the fluorescence wavelength or intensity emitted from said second fluorescent label created upon formation of complexes having antigens bound to the plurality of antibody-bead complexes and having said second fluorescent label using a flow cytometer by determining a ratio of fluorescence signal between the fluorescent antibody-bead complex and the fluorescent antigen in the complex of the fluorescence of any of said first fluorescent labels and said second fluorescent label.

2. The method of claim 1, wherein the plurality of fluorescent antibody-bead complexes differ in their fluorescence intensity.

3. The method of claim 1, wherein the plurality of fluorescent antibody-bead complexes differ in their fluorescent emission wavelength.

4. The method of claim 1, wherein the second fluorescent label comprises a fluorescent antibiotic.

5. The method of claim 1, wherein the second fluorescent label comprises a DNA binding dye.

6. The method of claim 1, wherein the first fluorescent label and the second fluorescent label have different fluorescence intensities.

7. The method of claim 1, wherein the first fluorescent label and the second fluorescent label have different fluorescence emission wavelengths.

8. The method of claim 1, wherein the antigens are *Streptococcus pneumomae* antigens.

9. The method of claim 8, wherein detecting the formation of complexes having antigens bound to an antibody bead complex and having a second fluorescent label indicates a *Streptococcus pneumoniae* infection.

10. The method of claim 1, wherein the sample is a biological sample.

* * * * *

UNITED STATES PATENT AND TRADEMARK OFFICE
CERTIFICATE OF CORRECTION

PATENT NO. : 7,659,085 B2  Page 1 of 1
APPLICATION NO. : 10/259907
DATED : February 9, 2010
INVENTOR(S) : Martinez et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1458 days.

Signed and Sealed this

Thirtieth Day of November, 2010

David J. Kappos
*Director of the United States Patent and Trademark Office*